United States Patent [19]

Brain

[11] Patent Number: 5,711,293
[45] Date of Patent: Jan. 27, 1998

[54] FORMING TOOL FOR USE WITH A LARYNGEAL MASK

[76] Inventor: Archibald Ian Jeremy Brain, Sandford House, Fan Ct. Gardens, Longcross Road, Chertsey, Surrey KT16 0DJ, United Kingdom

[21] Appl. No.: 590,488

[22] Filed: Jan. 24, 1996

[51] Int. Cl.$^6$ ............................................. A61M 16/00
[52] U.S. Cl. .................... 128/200.24; 128/207.14; 128/206.21; 128/DIG. 26; 206/803
[58] Field of Search ..................... 128/200.24, 207.15, 128/207.14, 206.26, 206.28, 911, 912, DIG. 26, 206.21; 604/96, 97, 98, 99; 206/803, 575, 207, 223

[56] References Cited

U.S. PATENT DOCUMENTS

| | | | |
|---|---|---|---|
| 4,509,514 | 4/1985 | Brain | 128/207.15 |
| 4,995,388 | 2/1991 | Brain | 128/207.15 |

*Primary Examiner*—Vincent Millin
*Assistant Examiner*—William J. Deane, Jr.
*Attorney, Agent, or Firm*—Hopgood, Calimafde, Kalil & Judlowe

[57] ABSTRACT

A forming tool member which presents a contoured peripherally continuous concave recess within the confines of an exposed upper surface of the tool. This concave recess conforms generally to the contour of the inflatable ring of a laryngeal mask in its inflated state. A second or closure member (or force-application member) has a convexly contoured lower peripheral surface conforming generally to a predetermined or desired optimum shape of the ring in its deflated state, so that the predetermined shape of the deflated ring can be achieved by squeezing compression of these two members against an interposed deflatable ring in the course of fully deflating the ring. Releasably engageable elements of the two members retain a clamped and compressed condition of the fully deflated ring, in instant readiness for emergency use of the involved laryngeal mask.

30 Claims, 4 Drawing Sheets

FORMING TOOL FOR USE WITH A LARYNGEAL MASK

BACKGROUND OF THE INVENTION

The invention relates to laryngeal masks of the variety wherein a backplate of generally elliptical configuration is surrounded by and peripherally continuously connected to an inflatable annular ring that is also of generally elliptical configuration and wherein an airway tube connected to the backplate will establish an exclusive passage to the trachea, once the ring has been inflated into sealed relation with the laryngeal inlet.

U.S. Pat. Nos. 4,509,514 and 4,995,388, and pending U.S. patent applications Ser. No. 07/869,491, filed Apr. 20, 1992, and Ser. No. 08/060,167, filed May 7, 1993 illustratively describe laryngeal masks of the character indicated.

A problem exists in the careless or unskilled attempted use of such masks, in that they must be deflated for insertion through a patient's mouth and into the pharynx, with correctly located insertional engagement of the distal end of the inflatable ring at the upper oesophageal sphincter. Subsequent inflation of the ring establishes the desired ring seal to the laryngeal inlet, thus also establishing the sealed exclusive airway passage to the trachea. The problem arises from the fact that an unskilled or careless user of the laryngeal mask may not be able to achieve a correctly collapsed shape of the inflatable ring, so that the distally projecting end of the inserted mask may not be able to exhibit a sufficient range of compliantly loaded piloting engagement with the back wall of the pharynx to avoid reversal of the distal end of the collapsed ring, thus increasing the difficulty of establishing mask location at the upper oesophageal sphincter.

U.S. patent application, Ser. No. 07/922,132, filed Jul. 30, 1992, addresses the foregoing problem by constructing a fillet of elastomeric adhesive in the peripheral valley defined by juncture of the backplate to the inflatable ring. The fillet is on the backside of the mask, and the fillet laps adjacent regions of the inflatable ring and of the backplate, the same being applied when the ring is in its inflated state. Thereafter, when the ring must be deflated for installation in a patient, the fillet preferentially biases the upwardly flared shape of the deflated ring such that chances of resilient reversal of the distal end of the mask are materially reduced. But resort to a perceived need to create such a fillet represents a secondary operation which calls for an expense that should be avoided.

BRIEF STATEMENT OF THE INVENTION

It is the principal object of the invention to provide an improved means of assuring against inadvertent compliant inversion of the distal end of a deflated laryngeal mask of the character indicated, in the course of manipulated insertion of the mask through a patient's throat and into the intended reference location, namely, the location determined by distal-end mask engagement with the upper oesophageal sphincter.

It is a specific object to achieve the above object with a tool which will quickly and optimally shape the inflatable ring in the course of deflating the same.

Another specific object is to meet the above objects as well as to provide compact and readily portable means for retaining a correctly deflated and shaped inflatable ring, in instant readiness for emergency use.

A further object is to provide a means of assured correct use of a laryngeal mask of the character indicated wherein the use is by persons having less than the best professional skill.

A general object is to meet the above objects with an accessory tool that enables effective use of laryngeal masks of less expensive construction.

Another object is to provide a tool meeting the above objects as part of a sealed package which contains a sterilized laryngeal mask in correctly deflated shape, in instant readiness for emergency use.

The invention in a preferred embodiment achieves these objects and certain further advantages over prior practice, by providing a forming tool member which presents a contoured peripherally continuous concave recess within the confines of an exposed upper surface of the tool. This concave recess conforms generally to the contour of the inflatable ring of the mask in its inflated state. A second or closure member (or force-application member) has a convexly contoured lower peripheral surface conforming generally to a predetermined or desired optimum shape of the ring in its deflated state, so that the predetermined shape of the deflated ring can be achieved by squeezing compression of these two members against an interposed deflatable ring in the course of fully deflating the ring. Releasably engageable elements retain a clamped and compressed condition of the fully deflated ring, in instant readiness for emergency use of the involved laryngeal mask.

BRIEF DESCRIPTION OF THE DRAWINGS

The invention will be described in detail in conjunction with the accompanying drawings, in which.

Figures 1, 2:
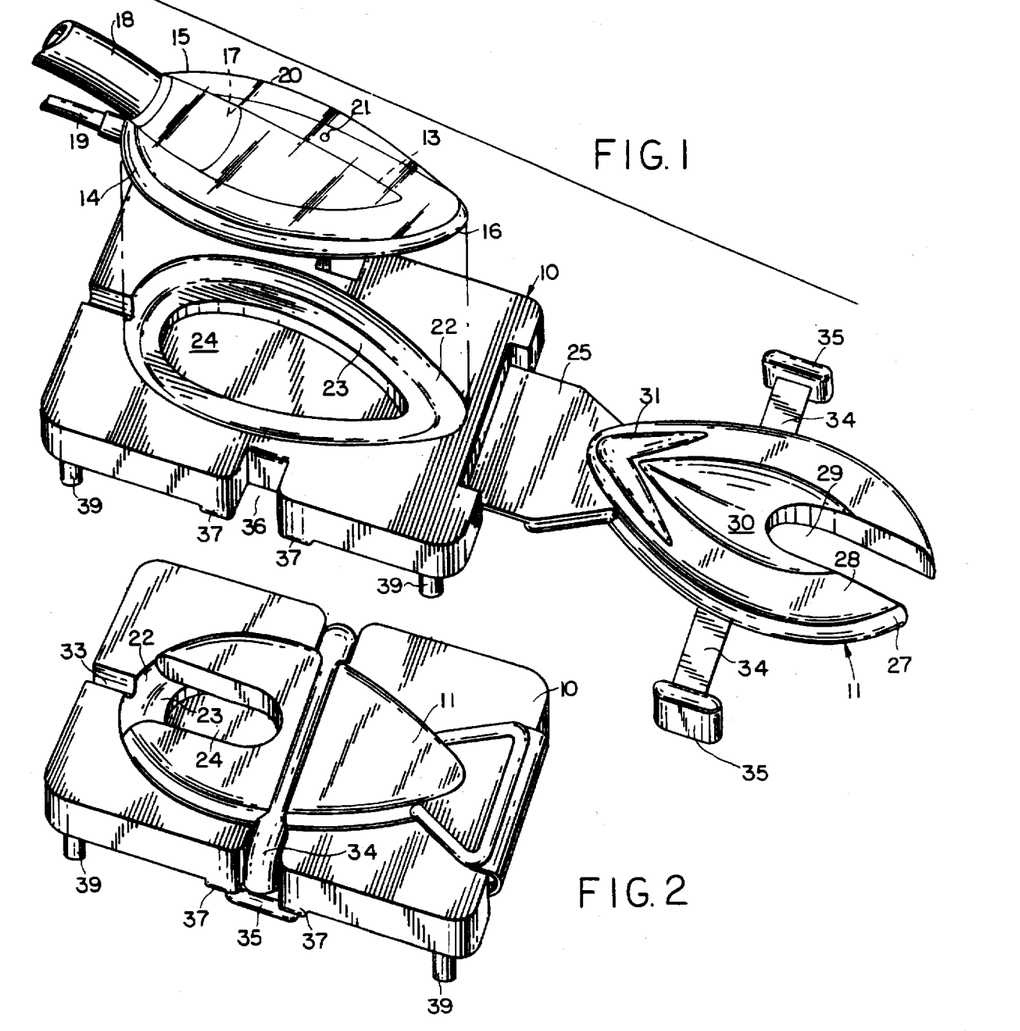
FIG. 1 is a perspective view of a preferred tool embodiment of the invention, in open condition and in readiness to receive the placement of a laryngeal mask thereon, the laryngeal mask being shown in inflated condition and in exploded relation to a base part of the tool.
FIG. 2 is a similar view of the tool of FIG. 1, in folded and clamped condition, but without a laryngeal mask assembled thereto.

Referring initially to FIGS. 1 and 2, the invention in its presently preferred embodiment is a forming tool comprising a base member 10 and a closure or force-application member 11 that are configured for accommodation of and operation upon a laryngeal mask 12. The mask 12 is shown only for the portion thereof which is to be installed in the pharynx of a patient and sealed to the laryngeal inlet. Specifically, the mask 12 is of currently preferred construction, wherein a backplate 13 is surrounded by and has peripherally sealed connection to an inflatable ring 14; both the backplate and the inflatable ring are of elongate generally elliptical contour, with a more rounded proximal end 15 and a more pointed distal end 16. The backplate 13 has a formation 17 that rises from one side of the general plane of ring 14 and at an acute angle to said plane near the proximal end 15, with connection to an airway tube 18, for airway passage through the backplate and exclusive airway communication with the trachea, when the mask has been sealed to the laryngeal inlet. The inflatable ring 14 has a flexible-tube connection 19 to the proximal end 15 for inflation/deflation purposes, and a two-way check valve (not shown) will be understood to. Serve for retention of the inflated condition of ring 14 or of its deflated condition, as may be required in use of the mask. In keeping with current preference, a thin flexible membrane 20 is inflatable (or deflatable) via an aperture 21 in ring 14, as and when ring 14 is inflated or deflated. For its installed position in a patient, the inflation of membrane 20 establishes a mask stabilizing reference against the back wall of the pharynx, with pneumatic forward loading of the inflatable ring 14 into enhanced sealing engagement with the laryngeal inlet, all as more fully described in said pending application Ser. No. 08/060,167, filed May 7, 1993.

As shown, the base member 10 is a relatively solid prismatic block with a flat upper surface. A contoured peripherally continuous concave recess is formed in and within the confines of this upper surface. The outer concave curvature 22 of this recess conforms generally to the outer convex curvature of the underside of ring 14, when in its inflated state. The outer concave curvature 22 is radially inward, as a function of depth of the recess, and this inward curvature concludes with tangency to a flat ledge or shoulder feature 23 of the recess. Within shoulder feature 23, the recess is further deepened at 24, and all features 22, 23 and 24 of the recess have peripheral limits which are in general conformance to the generally elliptical contour of ring 14. Specifically, and for a purpose which will become clear from explanation below, the radially inner and outer dimensions (i.e. the effective location and generally radial width) of shoulder 23 are such as to assure shoulder 23 registration with the peripheral contour of backplate 13 and with its peripherally continuous connection to ring 14, it being noted that in the inflated condition shown in FIG. 1, the plane of connection of backplate 13 to ring 14 is at vertical offset from the lower limiting geometric plane that is tangent to ring 14 in its inflated condition. It is also noted that, preferably, the recess depth from the upper surface of base member 10 to the plane of shoulder 23 is substantially equal to the above-noted vertical offset $T_1$, which is substantially one half the vertical or thickness dimension $T_2$ of ring 14 in its inflated condition, said thickness dimensionings being identified specifically in FIG. 5.

The other member of the tool of FIGS. 1 and 2, namely, the closure or force-application member 11, may be a separate part having fastening formations coacting with suitable formations of base member 10 for selective retention of a clamped squeezing of ring 14 between members 10 and 11. However, in the form shown, members 10 and 11 are integrally connected products of a single molding operation, as of suitable elastomeric material, wherein a thin and therefore relatively flexible connecting strip 25 serves a hinge function for articulated inversion of member 11, from its FIG. 1 position of longitudinal offset from base member 10 to its force-application or closure position of registration with the described recess formation features of base member 10. In FIG. 2, it will be understood that a laryngeal mask, such as mask 12 of FIG. 1, will have been positioned between base member 10 and closure member 11, for achieving a predetermined formed shape of ring 14 in its fully deflated state; however, interposed mask structure has been omitted in FIG. 2, for purposes of clarity.

As shown, the closure member 11 is relatively thick, although not as thick and bulky as base member 10. In its closed position (FIG. 2), the lower surface of member 11 is peripherally defined and convexly contoured for nested reception in the recessed features of the upper surface of base member 10; the features of this lower surface are seen, face-up, in the open tool condition of FIG. 1. These features include a convex periphery 27 which curves radially inward as a function of nested depth in the recess of base member 10 and a flat lower surface portion 28 which is tangent to the convex peripheral curve 27, it being intended that the flat surface portion 28 shall register with the flat shoulder surface 23, when in the "closed" condition of FIG. 2; in this closed condition, the convex curve of periphery 27 is preferably at clearance offset from the concave peripheral curve 22 of the base-member recess, to the extent of no more than twice the material thickness of the inflatable ring 14. A deep slot 29 has slightly divergent walls to engage and centrally locate member 11 as it is folded over a laryngeal mask in the direction of FIG. 2, the slot formation 29 engaging and locating against opposite sides of the airway connecting portion 17 of backplate 13; and within the generally elliptical inner contour of the flat surface portion 28, member 11 is recessed with a concave curvature 30, in general accordance with and adapted for locating engagement to the convex external profile of the airway connecting portion 17. Finally, at the hinged distal end of closure member 11, a V-shaped ridge 31 rises out of the plane of surface 28 to a distal maximum, for a purpose to be explained in connection with FIGS. 6 and 7.

Description of the tool of FIGS. 1 and 2 is completed by identifying a local groove or recess 33 in the center of the proximal end of the upper surface of base member 10; the inflation-air tube 19 and its connection to ring 14 have locating reception in groove 33. And to secure the clamped squeezing closure of members 10 and 11 on an interposed mask ring 14, member 11 is shown with integrally formed and outwardly projecting flexible straps 34, having enlarged terminal lugs 35; it is preferred that the length of straps 34 shall be such as to require a relatively tight stretching tension in each of the straps 34, in order to develop tensed lug-35 retention against the underside of base member 10, with straps 34 located in the base-body slots 36, it being noted that integral rib formations 37, local to the outer limits of the walls of slots 36, provide a local detent action for enhanced assurance of a releasable lug-35 clamped closure of the parts as shown in FIGS. 2. Spaced feet 39 formed in the underside of base member 10 provide ample clearance for manipulation of lugs 35 into clamping position while the tool is resting on the supporting surface of a table or counter.

Figures 3, 4:
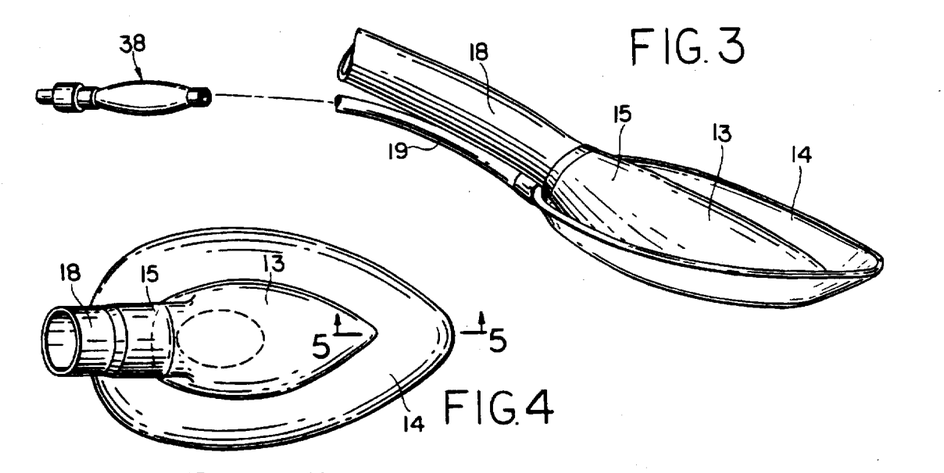
FIG. 3 is a perspective view of a deflated laryngeal mask that has been shaped by the tool of FIGS. 1 and 2.
FIG. 4 is a plan view of the laryngeal mask of FIG. 3, in inflated condition.
Figure 5:
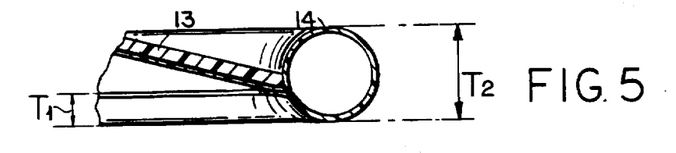
FIG. 5 is an enlarged fragmentary vertical section of the distal end of the laryngeal mask of FIG. 4, taken at 5—5 in FIG. 4.

Before describing action of the tool of FIGS. 1 and 2 on an interposed laryngeal mask, reference is made to FIGS. 3, 4 and 5, wherein FIG. 3 shows the desired upwardly flared shape or lip to which ring 14 is to be shaped by tool action, in conjunction with a deflation of ring 14, it being noted that one of the check valves within a fitting 38 in the inflation/deflation line 19 will hold the deflated state of ring 14. It will be noted also in FIG. 3 that the upper peripheral rim of the deflated ring is smoothly continuous, a condition that to date has been difficult if not impossible to attain, without a combination of luck and skill, factors that are seldom available. Nevertheless, the tool of the invention permits reliably repeatable formation of a smoothly continuous deflated ring, as shown. In contrast, the wrinkles and buckling seen in the drawings of said pending application Ser. No. 07/922,132 illustrate, by comparison, the hitherto best-attainable shape of a deflatable ring. To achieve the desired deflated shape, it is observed from FIG. 5 that, in inflated condition, the distal end of ring 14 is of generally circular section, and that a similar circular shape also exists for any section taken in a plane normal to a local plane of tangency to the inflated generally elliptical periphery of ring 14.

Figure 6:
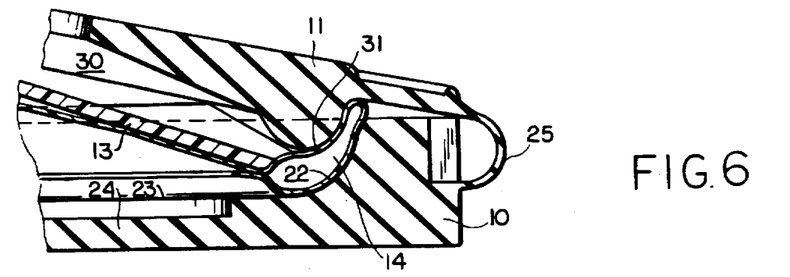
FIG. 6 is the first of a sequence of similar views taken at the section plane 5—5 of FIG. 4, for operation of a forming tool of the invention, to show an intermediate relation of the tool components in the course of a forming operation on the inflatable mask of FIGS. 4 and 5.
Figure 7:
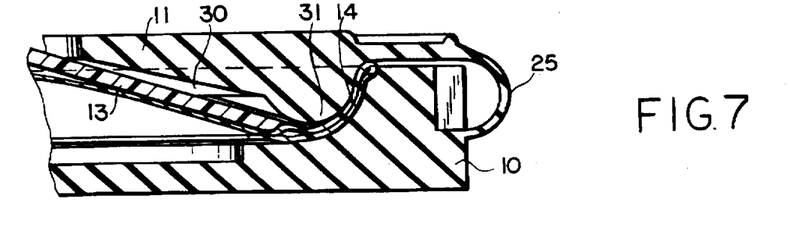
FIG. 7 is another view similar to FIG. 6, to show the relation of tool components at completion of the forming sequence.
Figure 8:
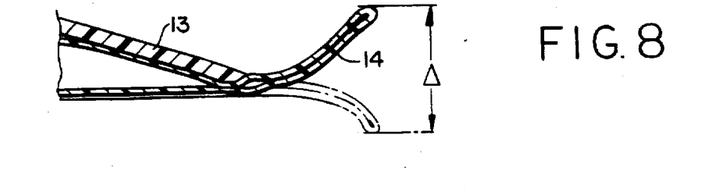
FIG. 8 is a view similar to FIGS. 6 and 7, i.e., in the plane 5—5 of FIG. 4, to show the distal end of the laryngeal mask, after forming and deflation and removal from the tool.

Referring now to FIGS. 6 and 7, it is seen that as closure member 11 is brought down onto an inflated laryngeal mask that has been positioned by the contoured recess of base member 10, the thickened distal end of the lower surface of member 11 first begins to indent and compress the distal end of ring 14 against the distal-end concave profile 22 of base member 10. Continued downward pressure on closure member 11 progressively pinches the distal end of ring 14 to the point where internal surfaces of the ring material are tightly engaged and can be caused to retain their tight engagement, by syringe or other deflation operation on the inner volume of ring 14. In the course of developing this squeeze of internal distal-end surfaces, the centrally recessed region 30 of closure member 30 engages and acts to depress backplate 13,.in reduction (to near zero) of the dimension $T_2$ of FIG. 5, as the peripheral junction of backplate 13 to ring 14 is compressed against the shoulder 23 of member 10. Once the compressed and fully evacuated condition is achieved (FIG. 7), the clamps 34, 35, 36 can be set to effectively hold a molded shape. And once removed from the tool, the vertical distal-end section has the appearance seen in FIG. 8, wherein internally engaged surfaces of ring material hold a normal shape which is illustrated by solid lines, and where a compliantly deflectable distal lip maintains its compliant nature throughout a deflection range $\Delta$, with enhanced resistance to lip inversion away from the lower limit shown for the range $\Delta$. This enhanced resistance is attributed (1) to the smoothly continuous flared contour and rim of the tool-formed and deflated mask ring 14, as seen in FIG. 3, and (2) to the tightly engaged internal surfaces of ring 14, particularly as developed at the more pointed distal-end 16 of ring 14.

On its way along a patient's airway to his pharynx, the flexible distal tip of the shaped and deflated ring 14 compliantly flexes in the range a as it tracks the patient's airway and the back wall of his pharynx, with substantially enhanced reliability of entry at the upper oesophageal sphincter, for mask location. Subsequent inflation air supplied as by a syringe fitted at 38 will then assuredly develop ring 14 in sealed relation with the laryngeal inlet and, if the mask is of the inflatable back-cushion variety shown in FIG. 1, the inflation will apply also to the volume beneath membrane 20, to enable cushion development against the back wall of the pharynx with resultant forward loading of the inflated ring in its sealing engagement with the laryngeal inlet.

Figures 9, 10:
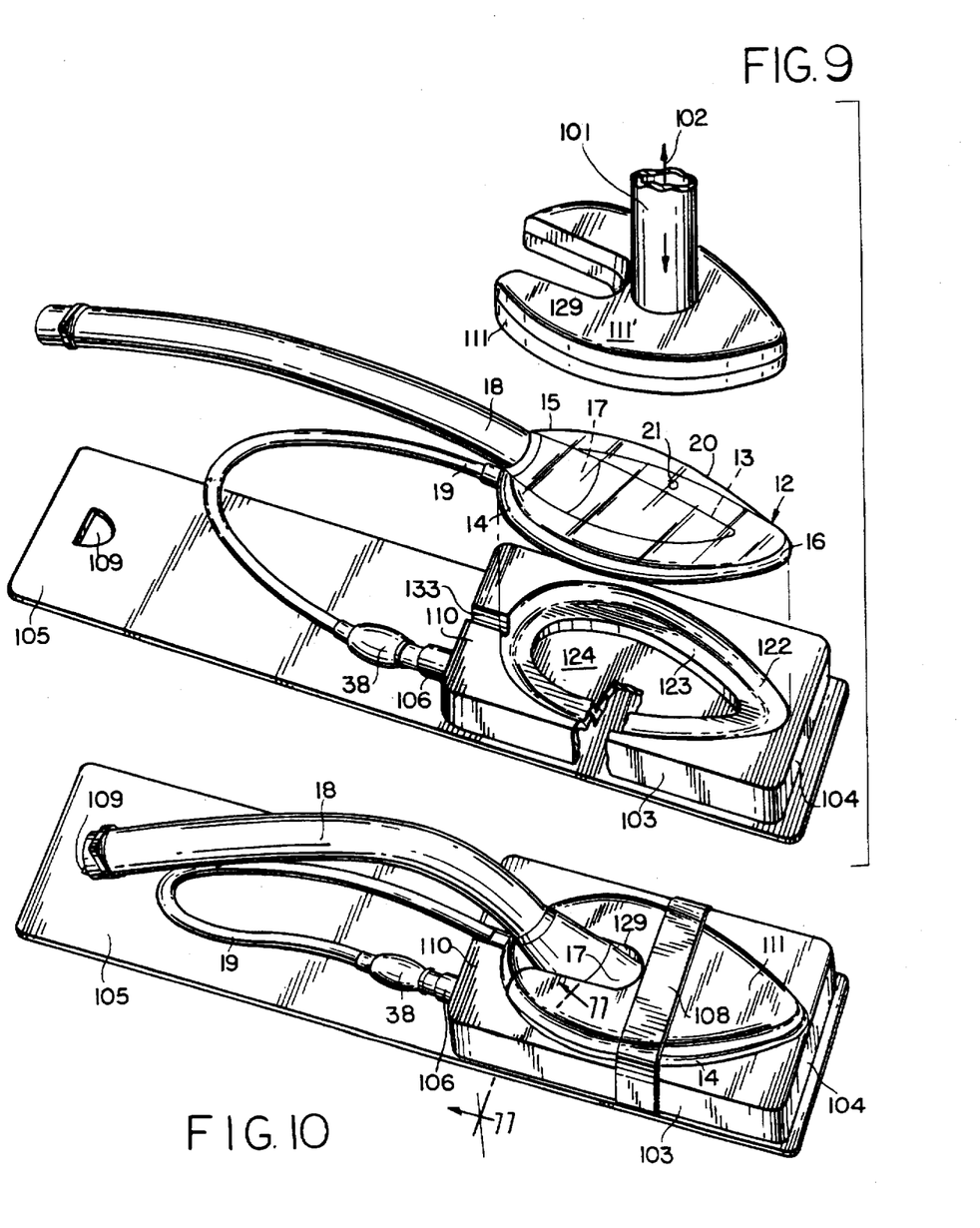
FIG. 9 is an exploded view in perspective to illustrate components of a package which incorporates forming-tool component features discussed in connection with the embodiment of FIGS. 1 and 2.
FIG. 10 is a view in the perspective of FIG. 9 to show the completed package.

FIGS. 9 and 10 are illustrative of an embodiment of the invention wherein the elements 11, 12, which have been described as parts of a forming tool for correctly shaping and retaining the deflated shape of a laryngeal mask, are in fact parts of packaging means for the laryngeal mask, in sealed and hygienically clean condition, in instant readiness for breaking the seal and immediately using the laryngeal mask. The use contemplated by such packaging importantly includes rescue squads whose business is to deal with emergencies, of life-and-death criticality, wherein time is of the essence.

In the exploded view of FIG. 9, the packaging means for laryngeal mask 12, including its airway tube 18, is seen to include a lower forming element 110 and an upper forming element 111, having confronting upper and lower forming profiles which accord with description above for the corresponding elements 10, 11 of FIGS. 1 and 2. The lower and upper forming elements 110, 111 of FIG. 9 could be hinge-connected, as in FIGS. 1 and 2, but this is not necessary for the packaging means of FIG. 9, which is likely to be discarded after removal of its contents. Thus, in FIG. 9, it is preferred that the lower and upper forming elements 110, 111 be separate parts. In this case, there must be means for manipulating the upper forming element 111, and in FIG. 9 a plate 111' will be understood to have a concave underside and to be manipulated by an upstanding tubular stem 101 having connection to suitably controlled evacuation means (not shown, but merely suggested by an arrow 102). Thus, on downward and correctly aligned depression of plate 111' and its vacuum-retained upper forming element 111, the correct convex annular forming features of element 111 are brought to bear on the inflatable ring 14 of mask 12 while the latter is seated on the concave annular forming features of the lower forming element 110, and while ring 14 is being deflated.

The lower forming element 110 is shown as the product of press-moulding from a single sheet of plastics material of sufficient thickness to provide firm support in reaction to the above-noted application of the upper forming element 111 to mask 12. As shown, the lower forming element 110 is of generally rectangular shape wherein side walls 102, 104 are peripherally continuous and are adapted to derive support from a flat platform or base plate 105, as of stiff plastics material or cardboard, with the depressed central region 124 sufficiently deep as to also derive support from the flat base plate 105. As a feature of packaging convenience, the lower forming element 110 is further seen to include a fitment formation 106, for detachable connection to the inflation/deflation tubing 19 of the laryngeal mask.

The full evacuation of ring 14 will be understood to occur at substantially the time when plate 111' has done its job and must be removed, by first relieving its vacuum hold on the upper forming plate 111. At this time, it is preferred to apply a continuous band 108 of heat-shrinkable material around the combined mid-section of the forming elements 110, 111, with the deflated mask ring therebetween, all as is depicted in FIG. 10 after transient localized application of heat or other radiation to shrink band 108 into tight retention of a sandwiched condition. In this condition, the air inlet formation 17 of the backplate of the mask projects upward through the slot 129 of the upper forming element 111, and the airway tube 18 curves downwardly into proximal-end location within a centering aperture 109 in base plate 105. FIG. 10 indicates a preference that, in the event of mounting to an elongate base plate (105), the peripheral dimensions of the base plate should exceed those of the combined plan view of the mask and of lower forming element 110, thus creating a margin around element 110 as clearly seen in FIGS. 9 and 10. The package is then completed by evacuated envelopment of the parts of FIG. 10 in suitably thin plastics material, which is preferably heat-shrinkable to assure hermetic sealing of all described parts. Emergency access is gained by merely ripping the thin plastics material.

Figure 11:
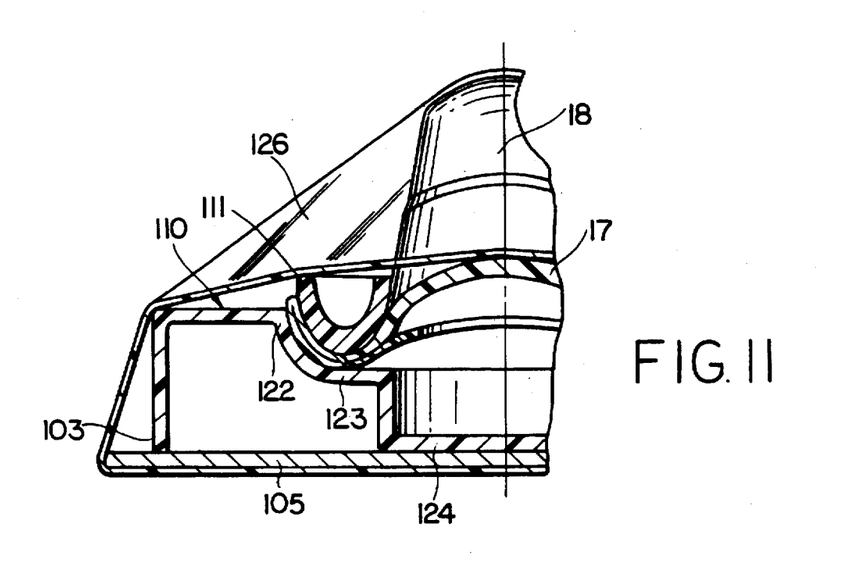
FIG. 11 is a fragmentary sectional view taken at 11—11 of FIGS. 10.

FIG. 11 is a fragmentary section taken at 11—11 of FIG. 10, to show the continuous nature of the thin plastics-material envelopment 126, it being understood that in the preferred evacuated condition of the completed package, certain areas of the enveloping thin plastics material will appear inwardly drawn or slumped, rather than straight, as shown.

Figure 12:
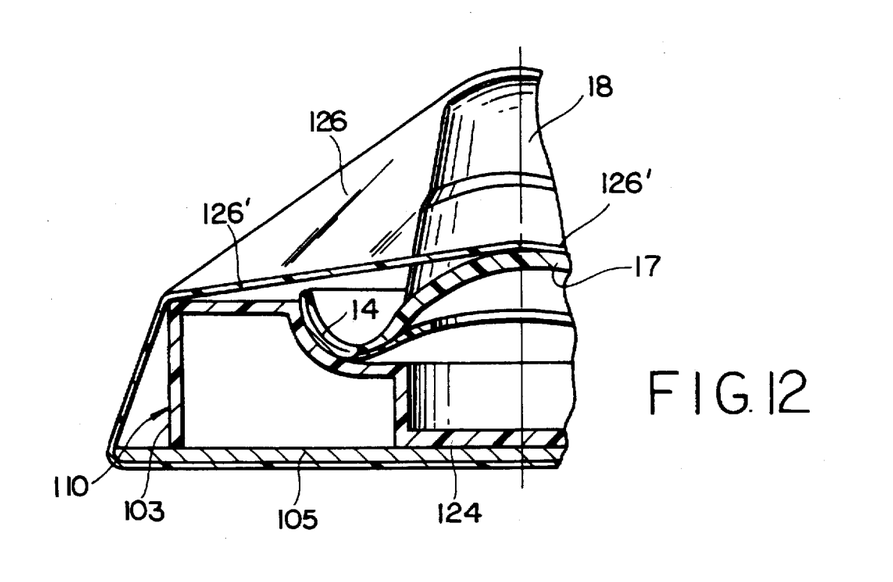
FIG. 12 is a view similar to FIG. 11, to show a modification.

FIG. 12 illustrates that, depending upon the inherent stiffness or bulk that may be embodied in the backplate 17 of the laryngeal mask, it may or may not be necessary to rely on an upper forming element 111 as packaging for the deflated ring 14 of the mask. That being the case for a sufficiently stiff backplate 17 in FIG. 12, upper forming element 111 has been omitted, and the shrunk envelopment material 126 is seen to provide a net downward force to the backplate 17, based on direct tie stretches 126' of envelopment material, extending symmetrically on opposite sides of the crown of backplate 17 to the outer upper corners of the elongate sidewalls 103 of the lower forming member 110.

While it has been indicated above that, for emergency usages, the described package with its one or more forming elements may be discarded, it is also contemplated that the described envelopment with thin plastics material may be applied to maintain the sterility and evacuated condition of a laryngeal mask retained by the clamped tool elements of FIGS. 1 and 2, suitably mounted to a base plate such as plate 105 of FIGS. 9 and 10. In that event, the tool of FIGS. 1 and 2 would be returnable for recycled use and packaging after autoclaving to assure sterility of the tool and of the evacuated mask that would be packaged therewith.

What is claimed is:

1. A tool for forming to a predetermined shape the fully deflated profile of a laryngeal mask, wherein the mask comprises an airway tube connected to a backplate having peripherally continuous connection in essentially a single plane to a surrounding inflatable peripheral ring which must be deflated for insertion in a patient via the throat, said ring having means for selective inflation thereof, to establish sealed airway-tube communication exclusively through the backplate to the trachea, said tool comprising:

a base member having a flat upper surface and a contoured peripherally continuous concave recess within confines of said upper surface, said recess conforming generally to the contour of said ring in its inflated state and on one side of said plane; and
 a closure member having a convexly contoured lower peripheral surface conforming generally to the predetermined shape of said ring in its deflated state and on the other side of said plane, said members being adapted for registration of their respective concave and convex contours with the ring of an interposed laryngeal mask, whereby the predetermined shape of the deflated profile can be achieved by squeezing compression of said members against the interposed ring in the course of fully deflating said ring.

2. The tool of claim 1, wherein the convexly contoured lower surface of said closure member is adapted for nested reception with peripheral clearance within the concave recess of said base member, in the absence of an interposed laryngeal mask.

3. The tool of claim 1, wherein said peripheral clearance is substantially equal to twice the thickness of the material of the inflatable ring.

4. The tool of claim 1, wherein said members are hingedly connected at a peripheral location which determines folded registration of said concave and convex contours.

5. The tool of claim 1, wherein said members have releasably engageable means for releasable retention of the squeezing compression of the interposed ring.

6. The tool of claim 4, wherein said members and their hinged connection are integrally related components of a single molded product of an elastomeric material.

7. The tool of claim 5, wherein said members and their releasably engageable means are integrally related components of a single molded product of an elastomeric material.

8. The tool of claim 1, wherein said members are hingedly connected at a peripheral location which determines folded registration of said concave and convex contours, and wherein said members have releasably engageable means for releasable retention of the squeezing compression of the interposed ring, and wherein said members and their hinged connection and their releasably engageable means are integrally related components of a single molded product of an elastomeric material.

9. The tool of claim 6, wherein said base member and said closure member are relatively thick and their hinged connection is a relatively thin strap formation.

10. The tool of claim 7, wherein said base member and said closure member are relatively thick and said releasably engageable means comprises at least one pair of relatively thick lug elements with relatively thin strap connection to laterally opposed peripheral locations on one of said members, the other of said members having opposed peripheral lug-engageable recess formations.

11. A tool for forming to a predetermined shape the fully deflated profile of a laryngeal mask, wherein the mask comprises an airway tube connected to a backplate having peripherally continuous connection in essentially a single plane to a surrounding inflatable peripheral ring which must be deflated for insertion in a patient via the throat:

said backplate and ring being of generally elliptical outer contour that is elongated between a more rounded proximal end a more pointed distal end and wherein the airway tube is connected at an acute angle to the proximal end of the backplate, said ring having means for selective inflation thereof to establish sealed airway-tube communication exclusively through the backplate to the trachea, said tool comprising:
 a base member having a flat upper surface and a contoured peripherally continuous concave recess within confines of said upper surface, said recess conforming generally to the contour of said ring in its inflated state and on one side of said plane;
 a closure member having a convexly contoured lower peripheral surface conforming generally to the predetermined shape of said ring in its deflated state and on the other side of said plane; and
 said closure member having an outwardly open slot at its proximal end, said slot being of width to straddle the airway backplate connection of the mask, and said members being otherwise adapted for registration of their concave and convex contours with the ring of an interposed laryngeal mask, whereby the predetermined shape of the deflated profile can be achieved by squeezing compression of said members against the interposed ring in the course of fully deflating said ring.

12. The tool of claim 11, in which said slot has outwardly divergent side walls adapted for lateral engagement with the airway-backplate connection of the mask for assuring the registration of said concave and convex contours with the interposed laryngeal mask at and near the proximal end of the mask.

13. The tool of claim 11, in which said members are hingedly connected at their distal ends when in folded registration of said concave and convex contours.

14. The tool of claim 11, in which said members have releasably engageable means for releasable retention of the squeezing compression of the interposed ring.

15. The tool of claim 14, wherein said releasably engageable means is in multiple and at spaced peripheral locations on said members.

16. The tool of claim 13, wherein the convexly contoured lower surface of said closure member is adapted for nested reception with peripheral clearance within the concave recess of said base member, in the absence of an interposed laryngeal mask, said clearance being of lesser magnitude near the distal ends of said concave and convex contours and of greater magnitude at regions other than near the distal ends.

17. The tool of claim 16, wherein said lesser magnitude clearance is less than twice the thickness of the material of said ring.

18. The tool of claim 16, wherein said greater magnitude thickness is substantially equal to twice the thickness of the material of said ring.

19. The tool of claim 11, wherein the generally conforming concave contour of said recess is curved radially inwardly as a function of depth of said recess, to a recess depth at which the radially inward concave curvature is substantially tangential to a flat radially inner surface portion of said base member; and wherein the convex contour of the lower surface of closure member is curved radially inwardly as a function of depth of reception in said recess, to a reception depth at which the radially inward convex curvature is in substantial tangency with a flat peripherally arcuate radially inner shoulder portion which is in relatively close clearance registration with the flat radially inner surface portion of said base member, and the lower surface of said closure member being further recessed within said shoulder portion in substantial conformance for nested engagement with the profile of the airway-backplate connection of an interposed laryngeal mask.

20. A tool for forming to a predetermined shape the fully deflated profile of a laryngeal mask, wherein the mask comprises an airway tube connected to a backplate having peripherally continuous connection in essentially a single plane to a surrounding inflatable peripheral ring which must be deflated for insertion in a patient via the throat, said backplate and ring being of generally elliptical outer contour that is elongate between a more rounded proximal end and a more pointed distal end and wherein the airway tube is connected at an acute angle to the proximal end of the backplate, said ring having means for selective inflation thereof to establish sealed airway-tube communication exclusively through the backplate to the trachea, said tool comprising:

a base member having an upper surface and a contoured peripherally continuous concave recess within confines of said upper surface, said recess conforming generally to the contour of said ring in its inflated state and on one side of and at substantially recess-depth offset from said plane, the generally conforming contour of said recess being curved radially inwardly as a function of depth of said recess, to a recess depth at which the radially inward concave curvature is substantially tangent to a flat radially inner surface portion of said base member;

and a force-application member having a lower surface with a concave formation conforming generally to the contour of said backplate on the opposite side of said plane and adapted for force application to a laryngeal mask having its inflatable ring nested in the concave recess of said base member, the lower surface of said force-application member being operative to displace the backplate of the mask in reduction of said offset and into abutment with the flat radially inner surface portion of said base member, whereby to collapse the inflatable ring upon subsequent deflation thereof, such that the collapsed ring is in the form of a peripherally continuous upwardly dished flare wherein inner-surface regions of the ring are in such relatively large-area frictional contact with each other as to provide non-inverting compliant piloting of the distal end of the dished shape in the course Of inserting a fully delated laryngeal mask into and along the back wall of the pharynx and into locating engagement with the oesophageal inlet.

21. The tool of claim 20, wherein the lower surface of said force-application member additionally includes a convexly contoured peripheral surface conforming generally to the predetermined shape of said ring in its deflated state and on the other side of said plane.

22. In combination, a package containing a laryngeal mask, wherein the mask comprises an airway tube connected to a backplate having peripherally continuous connection to a surrounding inflatable peripheral ring which must be correctly shaped and deflated for insertion in a patient, said package comprising upper and lower forming elements having complimentary upper and lower convex and concave annular surfaces for retaining the ring in its correctly shaped and deflated condition, and said package further including a sealed envelope surrounding said laryngeal mask and said forming elements in such circumferentially tensed condition as to compress said elements toward each other and in correctly shaped retaining relation with said inflatable ring.

23. The combination of claim 22, in which said package further includes a platform member of relatively stiff material having sufficient area and contour to support one of said forming elements as well as at least the proximal end of the airway tube, said sealed envelope being fully sealed around said mask and platform.

24. The combination of claim 22, in which said upper and lower elements are of relatively stiff molded-plastic construction, and a band of shrinkable plastic material circumferentially surrounding said elements and in shrunk condition for compressionally loading said elements in squeezed retention of the correctly deflated shape of said inflatable ring.

25. The combination of claim 24, in which said laryngeal mask includes a flexible-tube connection with check-valve means for retaining a given inflated or deflated state of said inflatable ring, said flexible tube connection having a proximal end that is adapted for removable connection to an external pressurizing and/or evacuating means, and in which one of said elements is formed with a local fitment to which the proximal end of said flexible tube is removably connected when said laryngeal mask is packaged and sealed.

26. In combination, a package containing a laryngeal mask, wherein the mask comprises an airway tube connected to a backplate having peripherally continuous connection to a surrounding inflatable peripheral ring which must be correctly shaped and deflated for insertion in a patient, said package comprising a forming element establishing a concave annular surface to which the laryngeal side of said inflatable ring must conform with the pharyngeal side of said inflatable ring in conforming adjacency to the laryngeal side when evacuated, and said package further including a sealed envelope surrounding said laryngeal mask and said forming element in such circumferentially tensed condition as to compress said element and said backplate toward each other and in correctly shaped retaining relation with said inflatable ring.

27. The combination of claim 26, in which said package further includes a platform member of relatively stiff material having sufficient area and contour to support said forming element as well as at least the proximal end of the airway tube, said sealed envelope being fully sealed around said mask and platform.

28. The combination of claim 26, in which said element is of relatively stiff molded-plastics construction, and a band of shrinkable plastics material circumferentially surrounding said element and in shrunk condition for compressionally loading said element in squeezed retention of the correctly deflated shape of said inflatable ring.

29. The combination of claim 28, in which said laryngeal mask includes a flexible-tube connection with check-valve means for retaining a given inflated or deflated state of said inflatable ring, said flexible tube connection having a proximal end that is adapted for removable connection to an external pressurizing and/or evacuating means, and in which said element is formed with a local fitment to which the proximal end of said flexible tube is removably connected when said laryngeal mask is packaged and sealed.

30. The tool of claim 1 and a package therefor, said base member and said closure member being in conforming retention of a correctly deflated inflatable ring of a laryngeal mask, and said package comprising a sealed envelope fully surrounding said members and said mask and compressionally loading said members into squeezing engagement with the ring in its deflated state.

* * * * *

UNITED STATES PATENT AND TRADEMARK OFFICE
CERTIFICATE OF CORRECTION

PATENT NO. : 5,711,293
DATED : January 27, 1998
INVENTOR(S) : Archibald Ian Jeremy BRAIN It is certified that error appears in the above-indentified patent and that said Letters Patent is hereby corrected as shown below:

Column 3, line 22;     after "understood" delete "to. Serve" and insert therefor --to serve--

Column 5, line 54;     after "range" delete "a" and insert therefor --Δ--

Column 10, line 15;    after "in the course" delete "Of" and insert therefor --of--

Signed and Sealed this

Twenty-ninth Day of September, 1998

*Attest:*

BRUCE LEHMAN

*Attesting Officer*     *Commissioner of Patents and Trademarks*